(12) United States Patent
Salaspuro et al.

(10) Patent No.: US 9,474,733 B2
(45) Date of Patent: *Oct. 25, 2016

(54) METHOD AND PREPARATION FOR BINDING ACETALDEHYDE IN SALIVA, STOMACH AND LARGE INTESTINE

(75) Inventors: Mikko Salaspuro, Helsinki (FI); Martti Marvola, Helsinki (FI)

(73) Assignee: BIOHIT OYJ, Helsinki (FI)

( * ) Notice: Subject to any disclaimer, the term of this patent is extended or adjusted under 35 U.S.C. 154(b) by 1219 days.

This patent is subject to a terminal disclaimer.

(21) Appl. No.: 10/415,422

(22) PCT Filed: Oct. 30, 2001

(86) PCT No.: PCT/FI01/00948
§ 371 (c)(1),
(2), (4) Date: Nov. 21, 2003

(87) PCT Pub. No.: WO02/36098
PCT Pub. Date: May 10, 2002

(65) Prior Publication Data
US 2005/0267042 A1   Dec. 1, 2005

(30) Foreign Application Priority Data
Oct. 30, 2000  (FI) ..................... 20002392

(51) Int. Cl.
| | | |
|---|---|---|
| *A01N 43/00* | (2006.01) | |
| *A61K 31/33* | (2006.01) | |
| *A01N 37/12* | (2006.01) | |
| *A01N 37/44* | (2006.01) | |
| *A61K 31/195* | (2006.01) | |
| *A61K 31/198* | (2006.01) | |
| *A61K 9/20* | (2006.01) | |

(52) U.S. Cl.
CPC ............ *A61K 31/198* (2013.01); *A61K 9/205* (2013.01)

(58) Field of Classification Search
USPC ................................. 514/183, 561
See application file for complete search history.

(56) References Cited

U.S. PATENT DOCUMENTS

| | | | | |
|---|---|---|---|---|
| 4,472,428 A | * | 9/1984 | Toru et al. ................ | 514/469 |
| 4,496,548 A | | 1/1985 | Moldowan et al. | |
| 4,528,295 A | * | 7/1985 | Tabakoff ..................... | 514/345 |
| 4,532,947 A | | 8/1985 | Caseley | |
| 4,844,905 A | * | 7/1989 | Ichikawa et al. ............ | 424/451 |
| 4,921,707 A | * | 5/1990 | Racz et al. ................... | 424/690 |
| 4,938,967 A | * | 7/1990 | Newton et al. .............. | 424/458 |
| 5,060,672 A | | 10/1991 | Irimi et al. | |
| 5,110,423 A | * | 5/1992 | Little et al. ................. | 205/254 |
| 5,169,638 A | * | 12/1992 | Dennis et al. ............... | 424/457 |
| 5,202,354 A | * | 4/1993 | Matsuoka et al. ........... | 514/562 |
| 5,695,781 A | * | 12/1997 | Zhang et al. ................ | 424/468 |
| 5,849,330 A | * | 12/1998 | Marvola et al. ............. | 424/472 |
| 5,922,346 A | | 7/1999 | Hersh | |
| 5,958,458 A | * | 9/1999 | Norling et al. .............. | 424/490 |
| 6,261,601 B1 | * | 7/2001 | Talwar et al. ............... | 424/469 |
| 6,299,867 B1 | | 10/2001 | Aoyagi et al. | |
| 6,635,273 B1 | * | 10/2003 | Loscalzo et al. ............ | 424/444 |
| 2005/0019427 A1 | | 1/2005 | Langeland | |

FOREIGN PATENT DOCUMENTS

| | | |
|---|---|---|
| EP | 0 234 464 A1 | 9/1987 |
| EP | 0504726 | 9/1992 |
| EP | 1238594 A2 | 11/2002 |
| JP | 62 277325 | 12/1987 |
| JP | 03-074327 A | 3/1991 |
| JP | 1991 136895 A | 3/1991 |
| JP | 04021635 | 1/1992 |
| JP | 61 16144 | 4/1994 |
| JP | 2003-055215 | 2/2003 |
| WO | WO 9915035 A1 | 1/1999 |
| WO | WO 99/27941 | 6/1999 |
| WO | WO 00/71145 | 11/2000 |
| WO | WO 02036098 A1 | 10/2002 |
| WO | WO 02/098405 | 12/2002 |
| WO | WO 2005/077464 | 2/2005 |

OTHER PUBLICATIONS

Jokelainen et al, *Alcoholism Clinical and Experimental Research*, 20(7):1206-1210 (1996).
Homann et al, *Carcinogenesis*, 21(4):663-668 (2000).
Sprince Herbert, et al., "Protection against Acetaldehyde Toxicity in the Rat by L-Cysteine, Thiamin and L-2-Methylthiazolidine-4-carboxylic Acid", Agents and Action, vol. 4/2 1974.
Database WPI, Section Ch, Week 198631, Derwent Publications Ltd., London, GB; AN 1986-201667, XP 002391658.
Salsapuro et al, *Annals of Medicine*, 28(3):195-200 (1996).
Salaspuro et al, *Int. J. of Cancer*, 97:361-364 (2002).
Salaspuro et al, *Best Practice and Res. Clin. Gastroenterology*, 17(4):679-694 (2003).
Salaspuro et al, *Critical Rev. in Clin. Laboratory Sciences*, 40(2):183-208 (2003).
Salaspuro et al, *Int. J. of Cancer*, 111:480-483 (2004).
Vakevainen et al, *Aliment Pharmacol. Ther.*, 14:1511-1518 (2000).
Vakevainen et al, *Rapid Communication*, 24(6):873 (2000).
Vakevainen et al, *Alcoholism: Clinical and Exp. Res.*, 25(3):421 (2001).
Vakevainen et al, *Scand. J. Gastroententerol*, pp. 649-655 (2002).

* cited by examiner

*Primary Examiner* — Marcos Sznaidman
(74) *Attorney, Agent, or Firm* — Sughrue Mion, PLLC

(57) ABSTRACT

The object of the invention is the use of compounds comprising one or more free sulphlydryl or amino groups for preparing a pharmaceutical composition for locally binding acetaldehyde in saliva, the stomach or the large intestine, and pharmaceutical compositions comprising the said compounds.

10 Claims, 2 Drawing Sheets

METHOD AND PREPARATION FOR BINDING ACETALDEHYDE IN SALIVA, STOMACH AND LARGE INTESTINE

The object of the invention is the use according to the preamble of claim 1 for preparing a pharmaceutical composition for locally binding the acetaldehyde in saliva, the stomach, and the large intestine. Another object of the invention is the pharma-ceutical compositions according to the preambles of claims 6, 11, and 19 and a method according to the preamble of claim 28 for decreasing the risk of developing cancer of the mouth, the pharynx, the oesophagus, the stomach, or the large intestine.

It has been found that acetaldehyde causes cancer in animals (Feron et al, (1982) Eur J Cancer Clin Oncol 18:13-31). It has also been found that acetaldehyde is a local carcinogen, when occurring in human saliva and the alimentary tract. This is supported by the fact that Asian heavy consumers of alcohol, who have a familial low-activity modification of aldehyde dehydrogenase-2 (ALDH2) enzyme, have both an increased risk of developing cancer of the mouth, the pharynx, and the alimentary tract, and an increased acetaldehyde content of the saliva after consuming alcohol (Väikeväinen et al, (2000) Alcohol Clin Exp Res 24:873-877).

In the organism, acetaldehyde is formed from alcohol as a consequence of hepatic metabolism and, according to recent research, locally in the alimentary tract through a microbial alcohol dehydrogenase (Salaspuro et al, (1996) Ann Med 28:195-200).

After moderate consumption of ethanol, for example, high acetaldehyde contents of a microbial origin have been found in human saliva; in other words, acetaldehyde builds up in saliva as an intermediate product of microbial metabolism (Homann et al, Carcinogenesis (1997) 18:1739-1743).

Acetaldehyde also builds up in the stomach-as a consequence of microbial metabolism in a situation, where there is no acid in the stomach or the acid has been removed by medication (Väkeväiinen et al, (2000) Alimentary Pharmacology Therapeutics, in press). It has also been shown that acetaldehyde builds up in the large intestine, because its bacteria that represent the normal flora are capable of converting ethanol into acetaldehyde (Jokelainen et al, (1996) Gut 39:100-104).

The average amount of saliva excreted by a human is 1.5 liters a day. The areas of influence of the acetaldehyde contained by the saliva include the mouth, the pharynx, the oesophagus, and the stomach.

The highest acetaldehyde contents of the organism in connection with consuming alcohol occur in the contents of the large intestine and in the saliva Endogenous ethanol, i.e., ethanol that builds up in the intestines in oxygen-free conditions as a consequence of microbes can also be found in the intestines. When this ethanol gets into contact with oxygen near the mucous membrane, for example, acetaldehyde is formed.

Acetaldehyde is also formed in the mouth, the pharynx, and the upper airways as a consequence of smoking and exposure to air contamination. It has been proven that chronic smoking increases the acetaldehyde production of saliva originated in microbes.

Pharmaceutical compositions containing the effective substances according to the present invention are known from before, the alleged effect of which is based on the reaction of the effective-substances to the acetaldehyde inside blood and/or cells. On the basis of prior art publications it is doubtful whether the preparations in question are even capable of decreasing the acetaldehyde content of blood originating in alcohol. The known preparations also have such a composition that they would not be able to bind, on a long-term basis, the acetaldehyde, which is locally generated in the organism and which locally occurs in high contents (see publications U.S. Pat. No. 5,202,354, U.S. Pat. No. 4,496,548, U.S. Pat. No. 4,528,295, U.S. Pat. No. 5,922,346).

The acetaldehyde, which forms in the organism during the consumption of alcohol and afterwards, also causes physiological symptoms called a hangover. Previously, an effort has been made to decrease the symptoms caused by acetaldehyde by taking preparations containing ascorbic acid, thiamine, cysteine or cysteic acid, and flavonoids or flavonoid complexes in a form of tablets swallowed orally in connection with, before or after consuming alcohol. It is believed that the method in question mostly decreases the acetaldehyde content in blood, because when swallowed, the effective substances go to the stomach and from there into the blood circulation. The tablets used in the method contained small amounts of effective substances only, and therefore had no effect on the acetaldehyde in saliva or the stomach (Matsuoka, U.S. Pat. No. 5,202,354 and Moldowan et al, U.S. Pat. No. 4,496,548).

It has been suggested that preparations containing amino acids, such as L-cysteine, methionine, taurine or arginine, ascorbic acid and vitamins A and E, which are sucked or chewed in the mouth be used to decrease the effect of the harmfuil free radical compounds that are formed in connection with using tobacco products or being exposed to them. It is believed that amino acids affect various tissues after being absorbed (Hersch, U.S. Pat. No. 5,922,346, Hersch, International Patent Application No PCT/US98/12617). However, the number of substances capable of binding the acetaldehyde and contained by these preparations is very low, the effect very short-term; hence, we are not talking about a local long-term effect.

So far, neither a method nor a preparation has been presented, which would locally decrease the acetaldehyde content of saliva, the mouth, the pharynx, the stomach or the large intestine. The methods and preparations according to prior art contain acet-aldehyde-binding substances in small amounts only, or their impact is very short-term, whereby the content of acetaldehyde quickly regains its previous level after the effect of the substances has ended.

The object of the invention is to provide a method and a preparation for decreasing or removing the acetaldehyde content of the saliva, and consequently, that of the pharynx, the oesophagus, the stomach, and separately that of the large intestine and the stomach from the area of the mouth and the alimentary tract and from the upper airways. The use, the composition, and the method according to the invention are very useful in locally binding the increased acetaldehyde that occurs in connection with consuming alcoholic drinks or smoking. In principle, the acetaldehyde can originate from any source, such as a foodstuff containing acetaldehyde; the acetaldehyde can have been formed from the ethanol contained by the foodstuff or it can have been formed from an endogenous ethanol occurring in the organism. The purpose of the invention is to decrease the risk of contracting cancers of the mouth and the alimentary tract, which are caused by the acetaldehyde in the said areas.

The invention is based on the surprising observation that the harmful amount of acetaldehyde locally occurring in saliva, the stomach or the large intestine can be bound locally, quicldy and in large concentrations into a chemically safe form by using the preparations according to the present invention. As the substances that bind it are released in contents high enough throughout the entire period of effect of the acet-aldehyde, the local acetaldehyde content remains low. In this way, the local risk of contracting cancer caused by acetaldehyde decreases.

To be more precise, the use according to the invention is characterized by what is stated in the characterizing part of claim 1.

According to the invention, compounds that comprise one or more free sulpbhydryl and/or amino groups are used to prepare a pharmaceutical compound, which is used to locally bind the acetaldehyde in saliva, the stomach or the large intestine.

Other objects of the invention are a pharmaceutical composition according to the characterizing part of claim 6 for binding acetaldehyde from saliva, a pharmaceutical composition according to the characterizing part of claim 11 for binding acetaldehyde from the stomach, and a pharmaceutical composition according to the characterizing part of claim 19 for binding acetaldehyde from the large intestine.

According to the invention, the pharmaceutical composition comprises one or more substances that bind acetaldehyde, as bound to a pharmaceutically acceptable carrier. The substances contained by the composition are selected so that the substances that are capable of binding acetaldehyde are released within a long period of time.

Another object of the invention is a method according to the characterizing part of claim 28 for decreasing the effect of acetaldehyde, which causes cancer, in human saliva, the stomach or the large intestine.

According to the method, the acetaldehyde contained by saliva, the stomach or the large intestine is locally bound into a safe form by using a pharmaceutical composition that releases one or more acetaldehyde-binding substances.

The invention provides considerable advantages. The pharmaceutical compositions comprising acetaldehyde-binding compounds can be used to decrease the risk of developing cancer of the mouth, the pharynx, the oesophagus, the stomach, and the large intestine. In particular, the compositions according to the invention can be used for large-scale consumers of alcohol and especially for those, who have a familial low-activity modification of the aldehyde dehydrogenase-2 (ALDH2) enzyme. The use of the compositions according to the invention is also of benefit to those who consume moderate amounts of alcohol or who consume foodstuffs that contain small contents of alcohol or acetaldehyde. Furthermore, the use of the compositions according to the invention also benefits smokers.

In the following, the present invention is examined more closely with the aid of a detailed description and examples. The appended drawing shows the measuring results of the acetaldehyde contents of the saliva of the test groups as the function of time, according to Example 1.

Figure 1:
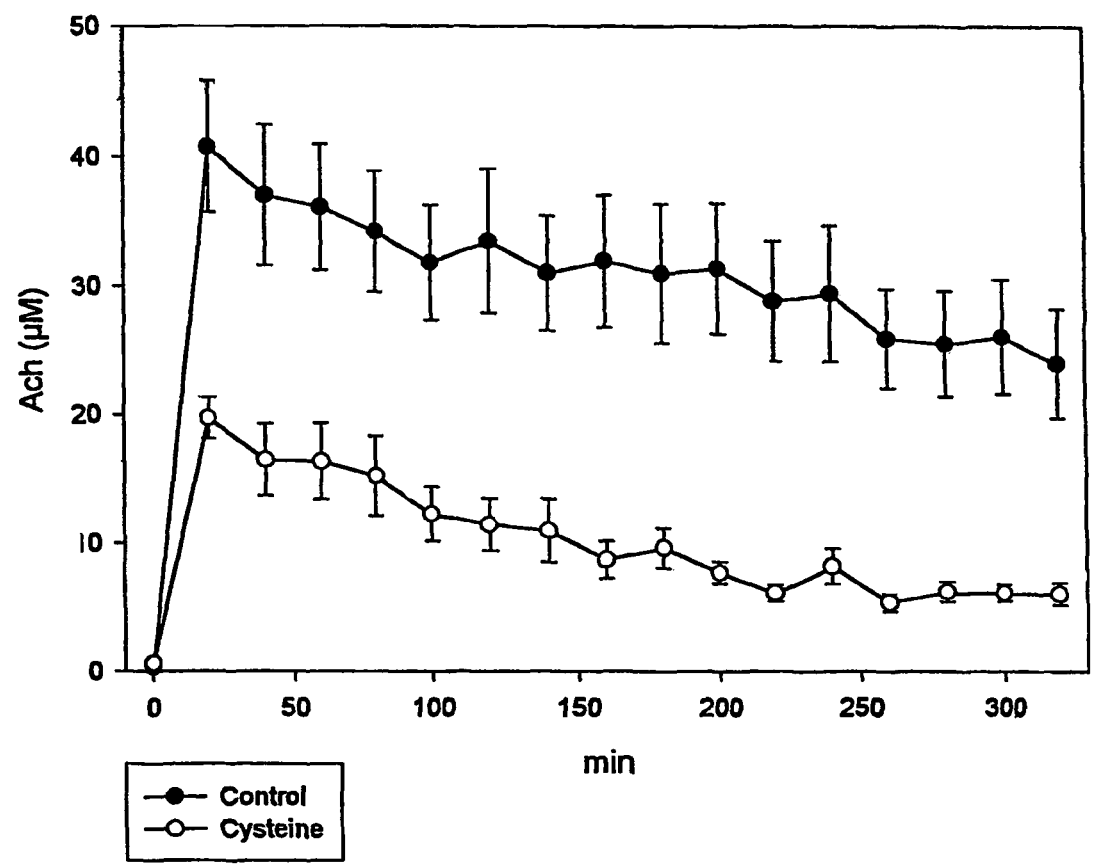
FIG. 1 shows the acetaldehyde content as the function of time in the saliva of the persons in a control group and that of the participants in the test group who used the acetaldehyde-binding preparation according to the invention.

"The acetaldehyde-binding substance" refers to a compound comprising one or more free sulphhydryl, amino or hydroxyl groups.

Cysteine and its derivatives are especially well suited to the purpose according to the invention. The most suitable amino acids for the use according to the invention are L and D-cysteines.

"The binding of acetaldehyde" refers to a chemical reaction between the acetaldehyde and the compound that has a free sulphhydryl and/or amino group, wherein the acetaldehyde jointly with the "acetaldehyde-binding substance" forms a larger molecule, and water can be formed in the reaction. For example, when reacting with cysteine, the acetaldehyde binds itself both to the sulphhydryl and the amino group and forms 2-methyl-L-thiazolidine4-carboxylic acid and water. The acetaldehyde can bind itself to the amino group of almost any protein, whereby Schiff's base or a 2-methyl-imidazole ring is formed.

According to the invention, the compounds obtained from acetaldehyde by chemically binding are safe for the organism.

Suitable compounds for binding acetaldehyde in the organism also include the compounds according to the formula (1):

(I)

wherein
$R^1$ is hydrogen or an acyl group with 1-4 carbon atoms,
$R^2$ is a sulphhydryl or sulphone group,
n is 1 or 2.

The substances according to the following formula are capable of binding acetaldehyde:

(II)

wherein R is derived from a protein (e.g., haemoglobin, albumin or tubuline)

In a reaction of the compound according to the formula (II) with acetaldehyde, a Shiff's base according to the formula (III) is formed,

(III)

wherein
R is derived from a protein (e.g., haemoglobin, albumin or tubuline).

Amino acids or other compounds that suitably bind acetaldehyde and comprise a free sulpbhydryl (SH) and/or amino ($NH_2$) group include:
L-cysteine,
D-cysteine,
Cysteic acid,
Cysteine glycine,
Threo or erythro-β-phenyl-DL-cysteine,
β-tetramethylene-DL-cysteine,
Methionine,
D-penicillamine and its dipeptides with N-terminals,
Semicarbazide,
Reduced glutathione,
β-mercaptoethylamine,
D,L-homocysteine,
N-acetylcysteine,
L-cysteinyl-L-valine,
β-β-tetramethylene-DL-cysteine,
Cysteinyl-glycine,
Mercaptoethylglycine,
Tre-(5)-β-phenyl-DL-cysteine, Erythro-beta-phenyl-DL-cysteine,
Thiaminhydrochloride,
Sodiummetabisulphite,
Arginine,
Glycine,
Lycine,
Mercaptanes.

However, only such acetaldehyde-binding compounds that cause no health hazard in the amounts according to the invention are suitable for the preparations according to the present invention.

"The long-term binding of acetaldehyde" means keeping the acetaldehyde content for at least 30 minutes, preferably over 60 minutes, and most preferably over 120 minutes below a limit that is considered harmful, or preferably on a lower level than in a case where no pharmaceutical composition is used.

"A harmful/carcinogenic content of acetaldehyde" in the human mouth, oesophagus, stomach, and large intestine is 20-800 µmol/l of saliva or the contents of the intestine.

Keeping the acetaldehyde content essentially lower than without the use of the pharmaceutical composition means keeping the acetaldehyde content at a level that is at least 20%, preferably over 40%, and most preferably over 60% lower than when not using the pharmaceutical composition.

Such a harmful or carcinogenic content of acetaldehyde in the human mouth, oesophagus, stomach or large intestine can be obtained in connection with consuming alcoholic drinks, particularly strong alcoholic drks, or foodstuffs containing alcohol, as a consequence of smoking or when consuming preparations containing acetaldehyde.

"Alcoholic drinks" are ethanol-containing drinks, the ethanol content varying within 0.7% by volume and 84% by volume."

"Alcoholic foodstuffs" refer to foodstuffs containing at least 0.7% of ethanol. Such foodstuffs can be, for example, fermented juices or preserves, or foodstuffs preserved with small amounts of alcohol, pastries, jellies, and mousse seasoned with liqueur or corresponding preparations containing alcohol.

The use of the preparations according to the invention can be of benefit even, when light alcoholic drks or foodstuffs are consumed, which contain small amounts of alcohol. Some foodstuffs can also already contain acetaldehyde. Acetaldehyde-containing foodstuffs, which have ethanol that is generated in connection with fermentation, such as beer, cider, wine, home-brewed beer, and other alcoholic drinks, as well as many juices. As for alcoholic drinks, sherry contains an especially large amount of acetaldehyde.

"In connection with consuming alcohol" herein refers to the period of time that begins from starting to enjoy alcohol and ends, when there is no more alcohol in the blood.

"In connection with smoking" herein refers to the period of time that begins from staring to smoke and ends, when smoking is stopped.

Pharmaceutical Preparation Affecting the Mouth

"A local, long-acting preparation that is placed in the mouth" refers to all preparations that are placed between the cheek or the lip and the gum, or preparations that are sucked or chewed in the mouth, and in which the release of the substance intended to have a local effect in the mouth, the pharynx, the oesophagus or the stomach is prolonged.

"A prolonged release of the effective substance" means that the release of the substance takes 30 minutes at the minimum, preferably 120 minutes at the minimum, most preferably over four hours. By using the compositions according to the invention, release times of the effective substance of as much as 4-8 hours can be achieved.

The compounds that are used in the preparation that binds acetaldehyde can be compounds comprising one or more free sulphhydryl and/or amino groups.

In addition to the acetaldehyde-binding, so-called effective substance(s), at least one substance that regulates the release rate of the effective substance is added to the locally long-acting pharmaceutical composition, which is placed in the mouth and can be in the form of a tablet. It is preferably that the composition also ensures that the preparation adheres to the mucous membrane of the mouth For these purposes, mostly two polymers are used, such as cellulose derivatives, chitosans, alginates, polyethylene glycols, carbomers or polycarbophils, preferably HPMC derivatives and carbomers, and most preferably a mixture of a HPMC-quality Methocel K4M and a carbomer-quality Carbopol 971, which are generally used as pharmaceutical additives, are known to be safe, and which in the physiological conditions of the mouth form a gel. With the aid of the substances used, both the release rate of the effective substance can advantageously be regulated and the adherence of the preparation to the mucous membrane of the mouth can be ensured. By varying the molecular size and the amount of polymers and, when using mixtures of various polymers, their mutual relationships, the release rate of the effective substance and the adhesion of the preparation to the mucous membrane can be regulated.

The total amount of polymers in the preparation is 10-50%, preferably 15-40%, and most preferably 20-30%.

A dosage unit of the pharmaceutical composition can comprise 50-500 mg of acetaldehyde-binding substance; preferably the amount of acetaldehyde-binding substance is 50-300 mg, and most preferably 100-200 mg.

In the oral conditions, preferably 15-25 mg of the compound is released in an hour.

The preparations according to the invention can be placed in the mouth 1 or 2 at a time and they can be replaced by new ones at 4 to 10-hour intervals, preferably at 6 to 8-hour intervals.

The composition of the long-acting tablet that is placed in the mouth can be as follows, for example:

| Acetaldehyde-binding substances | 100-200 mg |
|---|---|
| Non-ionised macromolecules | 20-50 mg |
| Ionising polymers | 6-10 mg |
| Lubricants | 1-3 mg |

Non-ionised macromolecules include, for example, methylcellulose (MC), hydroxypropylcellulose (HPC), and hydroxypropyl-methylcellulose (HPMC), and polyethylene glycol (PEG). Ionising polymers include, for example, sodium carboxy-methyl cellulose (NaCMC), alginic acid, sodium alginate, chitosan, polycarbophil (Noveon™), and cabomer (Carbopol™).

Pharmaceutical Preparation Affecting the Stomach

"A long-acting preparation that has a local effect on the stomach" refers to all monolithic or multiparticular tablets or capsules or granules as such, which, when wetted under the influence of the gastric juices adhere to the mucous membrane of the stomach or form a gel that floats in the contents of the stomach, as a consequence of which their residence time in the stomach is prolonged and thus enables a prolonged release in and a local effect of the drug on the stomach. The long-acting preparation that locally acts on the stomach can be a liquid preparation taken orally (mixture), the physical structure of which is a gel.

A special property required of the pharmaceutical composition that has a local effect on the stomach is that it remains in the stomach for as long as possible. Technically, this can be solved in two ways: by making a preparation that adheres to the mucous membrane of the stomach or making a preparation that floats in the contents of the stomach. The preparation can be rendered fixable to the mucous membrane of the stomach by using as additives cationic polymers, such as various chitosan grades. Preparations that float in the stomach are provided by using polymers (e.g., alginic acid) that form a gel and by adding to the preparation sodium hydrogen carbonate, which under the influence of gastric acid releases carbon dioxide, which in turn forms gas bubbles inside the gel. A liquid gel that floats in the stomach can also be prepared from sodium alginate, aluminium hydroxide, sodium hydrogen carbonate, and water, to which the acetaldehyde-binding compound can be added. A corresponding liquid preparation is also obtained by adding an acetaldehyde-binding substance to an aqueous dispersion of chitosan. Another preparation that remains in the stomach for a long time is a preparation, which is known as HBS™ (hydrodynamically balanced system). The preparation can remain in the stomach for a long time, when a relatively large tablet is made of it (with a diameter of at least 7-10 mm) and it is coated with a film, which does not decompose in the alimentary tract, and which, however, releases an effective substance (Oros™) through a hole which has been made to it, for example. However, a prerequisite is that such a preparation be consumed after eating.

A single dose of the pharmaceutical composition having a local effect on the stomach comprises 50-500 mg of acetaldehyde-binding substance; preferably the amount of acetaldehyde-binding.substance is 50-300 mg, and most preferably 100-200 mg.

When needed, the dosage is renewed at 4 to 10-hour intervals, preferably at 6 to 8-hour intervals.

The amount of compound released in the conditions of the stomach is preferably 40-80 mg in an hour.

The preparation according to the invention, which releases in the stomach, has at least one—often two—polymers, which have the task of keeping the chug as long as possible, for two hours minimum, in the stomach either so that it attaches the preparation to the mucous membrane of the stomach or forms a gel that floats in the contents of the stomach. Another task of the polymers is to prolong the release of the effective substance.

The preparation that locally binds acetaldehyde in the stomach can be a tablet that forms a gel in the stomach or a capsule comprising a mixture of powder or granules that forms a gel. In addition to the acetaldehyde-binding substances, the preparation comprises polymers that form a gel in the stomach, such as chitosans, alginates, sodium carboxy-methylcellulose grades, carbomers or aluminiium hydroxide. To advance floating in the stomach, the preparation can also comprise sodium hydrogen carbonate.

The amount of polymers in the preparation is 10-50%, preferably 15-40%, and most preferably 20-30%.

The amount of sodium hydrogen carbonate can be 10-30%, preferably 20% of the amount of polymers.

The preparation that locally binds acetaldehyde in the stomach can be a tablet or granule preparation, wherein the acetaldehyde-binding substance is mixed with the fillers needed and, after that, granulated by using enteric polymers as binders. The binder used can be any known enteric polymer, preferably a polymer with a solution pH of 6-7, and most preferably the polymer is any of the methacrylate derivatives, which are known by the trade names Eudragit L and Eudragit S. The amount of enteric polymer in the preparation is preferably 2-5%, most preferably 3-4%.

The preparation that locally binds acetaldehyde in the stomach can be a liquid preparation, i.e., a mixture comprising, in addition to the acetaldehyde-binding substance, also sodium alginate, aluminium hydroxide, sodium hydrogen carbonate, and water. The amount of water in the whole preparation is 70-90%, most preferably about 75-85%. The amount of sodium alginate in the preparation is preferably 2-10%, imost preferably about 5%, and the amount of aluminium hydroxide is preferably 5-15%, most preferably about 10%.

The relative composition of the preparation comprising granules can be as follows, for example:

| Acetaldehyde-binding substances | 60 parts |
| Chitosan | 10-40 parts |
| Calcium hydrogen phosphate | 0-30 parts |

The relative composition of the liquid preparation can be as follows, for example:

| Acetaldehyde-binding substances | 10 parts |
| Sodium alginate | 2-10 parts |
| Aluminium hydroxide | 5-15 parts |
| Sodium hydrogen carbonate | 1-2 parts |
| Water | 70-80 parts |

Pharmaceutical Preparation Affecting the Large Intestine

"A long-acting preparation that has a local effect in the large intestine" refers to all monolithic or multiparticular tablets or capsules or granules as such, which will not release the dose in a prolonged way until the preparation has drifted to the end of the small intestine or all the way to the large intestine.

The preparation according to the invention that releases acetaldehyde-binding substances in the large intestine in a prolonged way, carries the acetaldehyde-binding substance to the last part of the small intestine or to the large intestine before the substance in question is allowed to be released—whichever the releasing mechanism.

The pharmaceutical composition that binds acetaldehyde in the large intestine is administered orally. There are numerous techniques available for directing the release of an orally dosed drug to the large intestine. The most functional solutions are based on the use of enteric polymers. A film coating, which does not dissolve in the acidic environment of the stomach, but dissolves at a pH value of 7 at the latest, can be made both on the tablet and the granules. In making the preparation, it is also possible to use polysaccharides that degrade under the effect of microbes of the large intestine, or polymers generated by azo bonds. The form of preparation known by the trade name Oros™ can also be used, when its opening is first covered with an enteric polymer, the solution pH of which is ≈7.

Useful enteric polymers include, for example, the grades of hydroxypropyl methylcellulose-acetatesuccinate (HPMC-AS) sold by the trade name Aqoat™, Aqoat AS-HF™ in particular, a cellulose acetatephtalate (CAP) grade sold by the trade name Aquateric™, and methacrylic acid-methylmethacrylate copolymers, the grade sold by the trade name Eudragit-S™ in particular.

The preparation according to the invention has at least one ingredient, which adjusts the release of the effective substance not to take place until at the end of the small intestine or in the large intestine. This component can be a polymer that dissolves depending on the pH (=enteric polymer) or a polymer that degrades under the effect of the enzymes secreted by the bacteria of the large intestine. The polymer that controls the place of release can form a film around the entire preparation. It can also form a film around the particles (granules) contained by the multiple-part preparation. The polymer that degrades under the effect of the enzymes secreted by the bacteria of the large intestine can also be as a filler in a monolithic preparation, or as a filler in the granules or in a multiple-unit preparation prepared from these granules.

The preparation according to the invention is an enteric tablet, the film coating of which does not dissolve until at the end of the small intestine or at the begining of the large intestine. The dissolution pH of the polymer that forms the film is 6.0-7.5, preferably 6.5-7.0. The amount of enteric polymer that forms the film is 5-20%, preferably 10-15% of the whole mass of the tablet. The filler of the tablet can comprise pharmaceutical additives that do not swell, such as calcium hydrogen phosphate.

The preparation according to the invention can also be granules that comprise an acetaldehyde-binding substance and are coated with an enteric film, the dissolution pH of the film-forming polymer being 6.0-7.5, preferably 6.5-7.0. The amount of film-forming enteric polymer of the entire mass of the granule is 5-30%, preferably 15-25%. The granule can comprise 20-40%, preferably about 30% of filler poorly soluble in water, such as calcium hydrogen phosphate.

The binder of the granule coated with the enteric film, according to the invention, can be an enteric polymer, the dissolution pH of which is 6.0-7.5, preferably 6.5-7.0. The amount of binder in the granule is 2-5%, preferably 3-4%.

The preparation according to the invention can also be a tablet comprising the enteric coated granules described above, on which an enteric film has also been made. The tablet made for such a preparation not only comprises enteric granules, but also a filler suitable for direct compression, such as microcrystalline cellulose, the amount of which in the tablet is 30-70%, preferably 40-60%.

The dosage unit of the pharmaceutical composition-preferably comprises 50-500 mg of acetaldehyde-binding substance; preferably the amount of acetaldehyde-binding substance is 50-300 mg, and most preferably 100-200 mg.

The amount of compound releasing in the conditions of the large intestine is preferably 50-100 mg in an hour.

When needed, the dosage can be repeated at 4 to 10-hour intervals, preferably at 6 to 8-hour intervals.

The composition of the enteric tablet, which comprises enteric granules and binds acetaldehyde in the desired way, can be as follows, for example:

| Enteric granules: | Acetaldehyde-binding substance | 100 mg |
|---|---|---|
| | Filler, e.g., calcium hydrogen phosphate | 30-50 mg |
| | Enteric polymers | 40-60 mg |
| Enteric tablet: | Enteric granules | 170-210 mg |
| | Microcrystalline cellulose | 170-210 mg |
| | Lubricants (e.g. magnesium stearate and talcum) | 5-10 mg |
| | Enteric polymers | 30-50 mg |

Administration of Acetaldehyde-Binding Compositions

The content of acetaldehyde formed in saliva as a consequence of consuming alcoholic drinks, smoking or for some other reason can be decreased so that, for example, in connection with consuming alcoholic drinks or smoking, a preparation is placed in the mouth, under the upper lip, for example, which at a suitable rate releases cysteine or a similar acetaldehyde binding agents. In this case, the acetaldehyde content of saliva decreases by over 20%, preferably by over 40%, most preferably over 60%, typically by 60-80% compared with a placebo. For example, 100 mg of cysteine in the preparation is enough to have the desired effect for 4-5 hours. When needed, a new preparation is placed in the mouth after the previous one has dissolved. This is repeated as long as there is alcohol in the blood.

Similarly, the acetaldehyde content locally increased in the stomach as a consequence of consuming alcoholic drinks, for example, can be decreased by more than 20%, preferably over 40%, most preferably over 60%, typically 60-80% compared with a placebo by consuming, in connection with alcoholic drinks, a pharmaceutical composition that releases an acetaldehyde-binding compound at a suitable rate in the stomach.

According to the invention, the preparations that bind acetaldehyde and affect the mouth, the stomach, and the large intestine can also be used simultaneously.

The acetaldehyde content formed from consumed or endogenous ethanol in the large intestine can be decreased by over 20%, preferably over 40%, most preferably 60-80% compared with a placebo by consuming a preparation, which in the large intestine releases acetaldehyde-binding compounds at a suitable rate.

In the following, the invention is examined with the aid of examples.

EXAMPLE 1

Immediately before consuming an alcoholic drink, either a placebo or a preparation that slowly released cysteine at a suitable rate was attached to the gums under the upper lips of nine participants in a test. The amount of cysteine in the preparation was 100 mg. During 20 minutes, the participants consumed 0.8 g/kg of ethanol in the form of a drink containing 10% by volume of ethanol. During the next 320 minutes, the acetaldehyde contents of the saliva of the testees were measured at 20-minute intervals. The acetaldehyde contents of the saliva of the participants who used the cysteine-containing preparation was 3-5 times lower than that of the participants in the reference group during the entire measuring period. After consumption of alcohol, approximately 66% of the carcinogenic acetaldehyde could be removed by using an acetaldehyde-binding pharmaceutical composition. FIG. 1 shows the acetaldehyde content (Ach µmol/1) measured for the saliva of the control group testees (•) and the group, who used the preparation according to the invention (○), as a function of time (min).

EXAMPLE 2

The pharmaceutical composition placed in the mouth, which has a longterm local effect, can be prepared and used to decrease the risk of cancer caused by acetaldehyde as follows:

The composition of a capsule placed in the mouth can be as follows, for example:

| | |
|---|---|
| Cysteine | 100.0 mg |
| HPMC (Methocel K4M ™) | 30.0 mg |
| Carbomer (Carbopol 971P NF ™) | 6.9 mg |
| Magnesium stearate | 1.4 mg |

Cysteine, HPMC, and carbomer are mixed carefully by using mixers generally used in the pharmaceutical industry. At the final stage, nmagnesium stearate is also added to the mixture to function as lubricant of the mould of the tablet-compressing machine. Tablets (with a diameter of 9 mm) are compressed from the powder mixture by using conventional tablet machines.

The preparation is placed in the mouth in connection with consuming alcohol. As long as there is alcohol in the blood, a new capsule is taken after the previous one has dissolved.

EXAMPLE 3

The locally long-acting pharmaceutical preparation that binds acetaldehyde in the stomach can be prepared and used to decrease the risk of cancer caused by acetaldehyde as follows:

The relative composition of the preparation that locally binds acetaldehyde in the stomach can be as follows, for example:

| | |
|---|---|
| Cysteine | 60 parts |
| Chitosan | 10-40 parts |
| Calcium hydrogen phosphate | 0-30 parts |

The powder mixture is mixed by conventional mixers (such as a blender), which are used in the drug industry. After that, the powder mixture is granulated using a 2.5% acetic acid as a granulation liquid. The granulation liquid can be added to the same blender. The moist powder mass is compresses through a screen plate or a perforated plate (the diameter of the aperture being 2 mm). The formed granules are dried and screened. A screen fraction of 1.2-1.7 mm is recovered, which is dispensed into hard gelatine capsules so that the dose of cysteine is 100 mg.

The tablets prepared above are ingested to decrease the risk of cancer locally caused by acetaldehyde in occasions, which are favourable for an increase in the acetaldehyde content of the stomach, such as in connection with consuming alcoholic drinks. The dosage is given at 4 to 6-hour intervals as long as there is alcohol in the blood.

EXAMPLE 4

The pharmaceutical composition that releases acetaldehyde-binding substances in the large intestine in a prolonged way can be prepared and used to decrease the risk of cancer caused by acetaldehyde as follows.

The composition of the enteric tablet, which comprises enteric granules and binds acetaldehyde in the desired way, can be as follows, for example:

| | | |
|---|---|---|
| Enteric granules: | Cysteine | 100 mg |
| | Calcium hydrogen phosphate | 40 mg |
| | Eudragit-S | 5 mg |
| | Aqoat AS-HF | 40 mg |
| Enteric tablet: | Enteric granules | 185 mg |
| | Microcrystalline cellulose | 185 mg |
| | Magnesium stearate | 4 mg |
| | Talcum | 4 mg |
| | Aqoat AS-HF | 40 mg |

Cysteine and the calcium hydrogen phosphate that works as a fillg agent are mixed together. Eudragit S is dissolved in ethanol (a 20% solution) and the solution is used to moisten the powder mixture. The wet mass is compressed into granules. The dried granules are screened and a granule fraction of 1.2-1.7 mm is coated with Aqoat AS-HF. The composition of the coating solution is as follows: Aqoat AS-HF 10%, triethylcitrate 3.5%, magnesium strearate 3%, and water 83.5%. The coated granules are mixed with microcrystalline cellulose (e.g., Emcocel LP 200™) and, finally, the lubricants are added to the mixture: magnesium stearate and talcum. Next, the mixture is compressed into tablets and, finally; an enteric film is made on the tablet in the same way as on the granules. In all stages of operation, mixers, granulators, screening equipment, film coating equipment, and tablet compressing machines, which are generally used in the pharmaceutical industry, can be used.

The composition prepared above is ingested orally in connection with consuming alcoholic drinks. and the dosage is repeated at 4 to 6-hour intervals as long as there is alcohol in the blood.

EXAMPLE 5

In the trial, acetaldehyde was inactivated in vitro in the contents of the intestine by using the tablet according to the invention, which slowly released cysteine. The preparation was a compression-coated tablet, the coating material thereof being a polysaccharide, pectin, which degrades under the influence of microbes of the large intestine. The composition of the preparation used in the trial was as follows:
L-cysteine 100 mg
Pectin 190 mg
Microcrystalline cellulose 50 mg
Hydroxypropyl methylcellulose 100 mg
Polyvinyl pyrrolidone 42 mg
Talcum 2 mg
Magnesium stearate 2 mg Two volunteers participated in the trial, and the contents of their intestines were collected with the aid of Colonsteril intestine evacuation medicine. The obtained contents of the intestines (the excrement) were diluted with distilled water in a ratio of 1:1 to convert the excrement into a form, which is easier to process and is more soluble.

After this, the contents of the intestine were divided into four parts (1-4) 50 ml each. Ethanol was added to the samples, its final concentration thus being 35 mM in each sample.
1st sample=control without cysteine (contained additives of tablets, e.g., pectin)
2nd sample=100 mg of cysteine (i.e., one tablet)
3rd sample=300 mg of cysteine (i.e., 3 tablets)
4th sample=500 mg of cysteine (i.e., 5 tablets)

The samples were incubated (i.e., the conditions in question were maintained to cause a reaction) at a temperature of 37° C. in a water bath (corresponding to the temperature of the human body), slightly mixing all the time.

500-µl samples were taken from the excrement samples at about 1-hour intervals to analyse the concentrations of acetaldehyde and ethanol by gas chromatography. These samples were taken during a period of 600 minutes in total.

Figure 2:
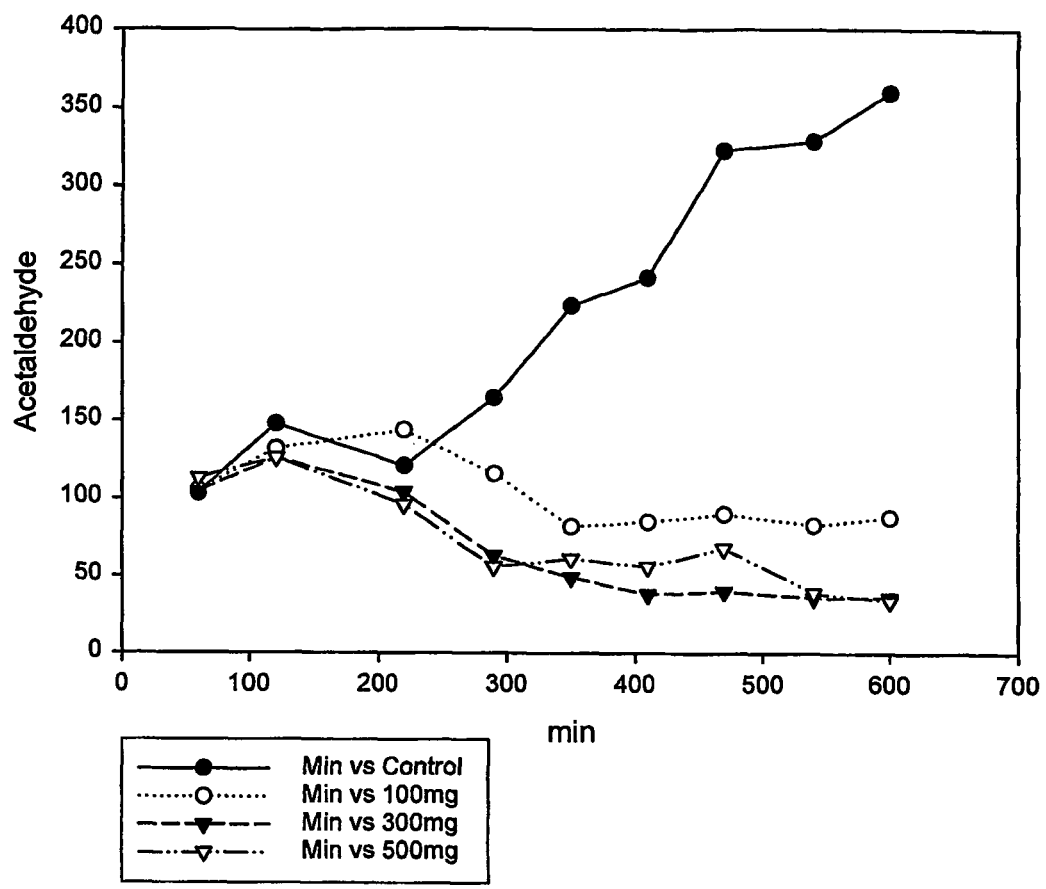
FIG. 2 shows the acetaldehyde content (μumol/l) of the contents of a human bowel as the finction of time in a control sample and in three samples, to which a preparation containing 100, 300, and 500 mg of an acetaldehyde-binding substance was added.

FIG. 2 shows the acetaldehyde content of the intestine (µmol/l) as the function of time in a control sample, to which no preparation according to the invention had been added, and in three samples, to which preparations containing 100, 300, and 500 mg of effective substance had been added. A 100-mg cysteine tablet decreased the amount of acetaldehyde in the samples by 51% compared with the control sample and, 300-mg and 500-mg tablets by 68% and 66%, correspondingly.

Thus, the response of the acetaldehyde content of the samples is a good indication of how the preparation according to the invention considerably decreases the acetaldehyde content generated from ethanol under the effect of microbes in the contents of the intestine. The conditions corresponded well to in vivo conditions.

It is especially surprising that the effective substance, which contains a very reactive SH group, reacts in the intestinal juice exactly as desired, i.e., the effective substance, for example, is not uselessly consumed in reactions with the other compounds of the contents of the intestine.

The invention claimed is:

1. A method for decreasing the risk of contracting cancer of the mouth, the pharynx, the oesophagus, the stomach or the large intestine caused by acetaldehyde produced by microbes from ethanol in saliva, the stomach or the large intestine, said method comprising administering to a subject, immediately before drinking alcohol, a sustained-release composition consisting essentially of:
   (A) 100 mg of L-cysteine, 30 mg of hydroxypropyl methylcellulose 6.9 mg of carbomer and 1.4 mg of magnesium stearate, that effects, in the mouth of a subject in need thereof, to achieve sustained release of the L-cysteine locally in the saliva for at least 30 minutes; or
   (B) 60 parts of L-cysteine, 10-40 parts chitosan, 0-30 parts calcium hydrogen phosphate, that effects, in the stomach of a subject in need thereof, to achieve sustained release of the L-cysteine locally in the stomach for 0.5 to 8 hours, wherein the composition is optionally dispersed in hard gelatin capsules containing about 100 mg of L-cysteine per single dose; or
   (C) 100 mg of L-cysteine, 5 mg of methacrylic acid-methylmethacrylate polymer, 40 mg of $CaHPO_4$, and 40 mg of hydroxypropyl methylcellulose-acetate succinate (HPMC-AS) that effects, in the large intestine of a subject in need thereof, to achieve sustained release of the L-cysteine locally in the large intestine for 0.5 to 8 hours.

2. The method according to claim 1, wherein said sustained-release composition continues to be administered as long as alcohol is consumed by the subject and/or ethanol therefrom is present in the blood of said subject.

3. The method according to claim 2, wherein said sustained-release composition is in the form of a tablet and is placed in the mouth of said subject during consumption of alcohol by said subject, and said tablet is administered at 4 to 10 hour intervals.

4. The method according to claim 3, wherein said sustained-release composition is in the form of a tablet and is placed in the mouth of said subject during consumption of alcohol by said subject, and said tablet is administered at 6 to 8 hour intervals.

5. The method according to claim 1, wherein the hydroxypropyl methylcellulose forms a gel in the mouth.

6. The method according to claim 1, wherein said sustained-release composition is granulated, and the solution pH of which is 6-7.

7. The method according to claim 1, wherein acetaldehyde binds to the L-cysteine through both the sulfhydryl and the amino group present in the L-cysteine.

8. The method according to claim 1, wherein the composition is a coated tablet, the coating thereof comprising the methacrylic acid-methylmethacrylate polymer, which is hydrolyzed in a solution having a pH value of 6.0-7.5.

9. The method according to claim 1, wherein said composition comprises granules, which are coated with the methacrylic acid methylmethacrylate polymer which is hydrolyzed in a solution with a pH value of 6.0-7.5.

10. A method for decreasing the risk of contracting cancer of the mouth, the pharynx, the oesophagus, the stomach or the large intestine, said method comprising administering to a subject immediately before drinking alcohol, a sustained-release composition consisting essentially of:
   (A) 100 mg of L-cysteine, 30 mg of hydroxypropyl methylcellulose 6.9 mg of carbomer and 1.4 mg of magnesium stearate, that effects, in the mouth of a subject in need thereof for binding acetaldehyde locally, and to render acetylacetaldehyde into a non-harmful form, to achieve sustained release of the L-cysteine locally in the saliva for at least 30 minutes; or
   (B) 60 parts of L-cysteine, 10-40 parts chitosan, 0-30 parts calcium hydrogen phosphate, that effects, in the stomach of a subject in need thereof for binding acetaldehyde locally, and to render acetaldehyde into a non-harmful form, to achieve sustained release of the L-cysteine locally in the stomach for 0.5 to 8 hours, wherein the composition is optionally dispersed in hard gelatin capsules containing about 100 mg of L-cysteine per single dose; or
   (C) 100 mg of L-cysteine, 5 mg of methacrylic acid-methylmethacrylate polymer, 40 mg of $CaHPO_4$, and 40 mg of hydroxypropyl methylcellulose-acetate succinate (HPMC-AS), that effects, in the large intestine of a subject in need thereof for binding acetaldehyde locally, and to render acetaldehyde into a non-harmful form, to achieve sustained release of the L-cysteine locally in the large intestine for 0.5 to 8 hours.

* * * * *